US008241353B2

(12) United States Patent
Deacon et al.

(10) Patent No.: US 8,241,353 B2
(45) Date of Patent: *Aug. 14, 2012

(54) ANGLE INDICATOR FOR OCULAR MEASUREMENTS

(75) Inventors: Jim Deacon, Goleta, CA (US); Edward Geraghty, Rancho Santa Margarita, CA (US); Edward Zaleski, Santa Ana, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/205,358

(22) Filed: Aug. 8, 2011

(65) Prior Publication Data

US 2011/0292336 A1 Dec. 1, 2011

Related U.S. Application Data

(63) Continuation of application No. 11/739,392, filed on Apr. 24, 2007, now Pat. No. 7,993,398.

(51) Int. Cl.
*A61F 2/14* (2006.01)
*A61F 2/16* (2006.01)
*A61B 5/103* (2006.01)
*A61B 5/117* (2006.01)

(52) U.S. Cl. ...... 623/5.12; 623/4.1; 623/5.11; 623/6.11; 600/587

(58) Field of Classification Search .................. 600/587; 623/5.11, 5.12, 6.11
See application file for complete search history.

(56) References Cited

U.S. PATENT DOCUMENTS

| 4,077,071 | A | 3/1978 | Freeman |
| 4,093,361 | A | 6/1978 | Erickson et al. |
| 4,134,160 | A | 1/1979 | Bayers |
| 4,174,543 | A | 11/1979 | Kelman |
| 4,249,272 | A | 2/1981 | Poler |

(Continued)

FOREIGN PATENT DOCUMENTS
DE   8107675 U1   7/1981
(Continued)

OTHER PUBLICATIONS

Alio J.L., et al.,"Phakic anterior chamber lenses for the correction of myopia: a 7-year cumulative analysis of complications in 263 cases," Ophthalmology, 1999, vol. 106 (3), pp. 458-466.

(Continued)

*Primary Examiner* — Jeffrey G Hoekstra
*Assistant Examiner* — Adam Eiseman
(74) *Attorney, Agent, or Firm* — Abbott Medical Optics Inc.

(57) ABSTRACT

Implantation of an accommodating intraocular lens in an eye may require the accurate measurement of the size, circumference, or diameter of the capsular bag of the eye. A flexible ring or ring portion may be temporarily or permanently inserted into the capsular bag for measuring the circumference of the capsular bag, for example, after extraction of a natural lens from the capsular bag. The ring or ring portion is generally compressible to fit through a surgical incision, then expands to fill the capsular bag along an equatorial region. The ring or ring portion includes a central component that changes shape and/or angle as the ring or ring portion is compressed. The shape change is generally correlated to the size of the capsular bag and may be visually measured through the cornea, the measurement being generally independent of corneal magnification. The measurement may be used to determine or calculate information about the capsular bag such as its size, elasticity, accommodative range, and so forth.

21 Claims, 6 Drawing Sheets

U.S. PATENT DOCUMENTS

| | | | |
|---|---|---|---|
| 4,254,509 | A | 3/1981 | Tennant |
| 4,254,510 | A | 3/1981 | Tennant |
| 4,316,293 | A | 2/1982 | Bayers |
| 4,319,564 | A | 3/1982 | Karickhoff |
| 4,370,760 | A | 2/1983 | Kelman |
| 4,377,873 | A | 3/1983 | Reichert, Jr. |
| 4,403,353 | A | 9/1983 | Tennant |
| 4,404,694 | A | 9/1983 | Kelman |
| 4,424,597 | A | 1/1984 | Schlegel |
| 4,446,581 | A | 5/1984 | Blake |
| 4,480,340 | A | 11/1984 | Shepard |
| 4,551,864 | A | 11/1985 | Akhavi |
| 4,556,998 | A | 12/1985 | Siepser |
| 4,560,383 | A | 12/1985 | Leiske |
| 4,605,409 | A | 8/1986 | Kelman |
| 4,605,411 | A | 8/1986 | Fedorov |
| 4,629,460 | A | 12/1986 | Dyer |
| 4,629,462 | A | 12/1986 | Feaster |
| 4,676,791 | A | 6/1987 | LeMaster et al. |
| 4,676,792 | A | 6/1987 | Praeger |
| 4,681,102 | A | 7/1987 | Bartell |
| 4,687,484 | A | 8/1987 | Kaplan |
| 4,687,485 | A | 8/1987 | Lim et al. |
| RE32,525 | E | 10/1987 | Pannu |
| 4,725,277 | A | 2/1988 | Bissonette |
| 4,734,095 | A | 3/1988 | Siepser |
| 4,781,717 | A | 11/1988 | Grendahl |
| 4,787,904 | A | 11/1988 | Severin et al. |
| 4,834,748 | A | 5/1989 | McDonald |
| 4,863,539 | A | 9/1989 | Lee et al. |
| 4,997,442 | A | 3/1991 | Barrett |
| 5,019,097 | A | 5/1991 | Knight et al. |
| 5,047,052 | A | 9/1991 | Dubroff |
| 5,071,432 | A | 12/1991 | Baikoff |
| 5,078,742 | A | 1/1992 | Dahan |
| 5,133,749 | A | 7/1992 | Nordan |
| 5,147,395 | A | 9/1992 | Willis |
| 5,147,397 | A | 9/1992 | Christ et al. |
| 5,197,981 | A | 3/1993 | Southard |
| 5,201,763 | A | 4/1993 | Brady et al. |
| 5,203,790 | A | 4/1993 | McDonald |
| 5,217,491 | A | 6/1993 | Vanderbilt |
| 5,225,858 | A | 7/1993 | Portney |
| 5,258,025 | A | 11/1993 | Fedorov et al. |
| 5,433,745 | A | 7/1995 | Graham et al. |
| 5,476,513 | A | 12/1995 | Brady et al. |
| 5,628,796 | A | 5/1997 | Suzuki |
| 5,691,800 | A | 11/1997 | Iki et al. |
| 5,716,403 | A | 2/1998 | Tran et al. |
| 5,801,807 | A | 9/1998 | Satake et al. |
| 5,928,282 | A | 7/1999 | Nigam |
| 6,015,435 | A | 1/2000 | Valunin et al. |
| 6,051,024 | A | 4/2000 | Cumming |
| 6,129,759 | A | 10/2000 | Chambers |
| 6,179,870 | B1 | 1/2001 | Sourdille et al. |
| 6,235,055 | B1 | 5/2001 | Chu |
| 6,261,321 | B1 | 7/2001 | Kellan |
| 6,319,282 | B1 | 11/2001 | Nishi |
| 6,419,697 | B1 | 7/2002 | Kelman |
| 6,598,606 | B2 | 7/2003 | Terwee et al. |
| 7,455,407 | B2 | 11/2008 | Neal et al. |
| 7,616,330 | B2 | 11/2009 | Neal et al. |
| 7,794,497 | B2 | 9/2010 | Brady et al. |
| 2001/0051825 | A1 | 12/2001 | Peterson |
| 2002/0173846 | A1 | 11/2002 | Blake et al. |
| 2004/0054358 | A1 | 3/2004 | Cox et al. |
| 2004/0068317 | A1 | 4/2004 | Knight |
| 2004/0167622 | A1 | 8/2004 | Sunalp et al. |
| 2005/0251254 | A1 | 11/2005 | Brady et al. |
| 2006/0020268 | A1 | 1/2006 | Brady et al. |
| 2007/0268453 | A1 | 11/2007 | Hong et al. |
| 2008/0018910 | A1 | 1/2008 | Neal et al. |
| 2008/0231809 | A1 | 9/2008 | Haigis |
| 2008/0269642 | A1 | 10/2008 | Deacon et al. |
| 2010/0130888 | A1 | 5/2010 | Deacon et al. |

FOREIGN PATENT DOCUMENTS

| | | |
|---|---|---|
| EP | 957331 A2 | 11/1999 |
| FR | 2745711 A1 | 9/1997 |
| WO | WO9856315 A1 | 12/1998 |
| WO | WO0135868 A1 | 5/2001 |
| WO | WO0154569 A1 | 8/2001 |
| WO | WO200603226 A2 | 3/2006 |

OTHER PUBLICATIONS

Apple D.J., et al, "Anterior Chamber Lenses Part 1: Complications and Pathology and a Review of Designs," Journal of Cataract Refractive Surgery, 1987, vol. 13 (2), pp. 157-174.

Apple D.J., et al., "Intraocular Lens Evolution, Designs," Complications and Pathology, 1989, vol. 22 (36), pp. 205-221.

Apple D.J., et al., "Intraocular Lenses: Evolution, Designs, Complications and Pathology," 1989, vol. 36 (1), pp. 22-36.

Apple D.J., et al. Intraocular Lenses: Evolution, Designs, Complications and Pathology, Williams & Wilkins, 1989, pp. 205-221.

Baikoff G., et al., "Angle-fixated Anterior Chamber Phakic Intraocular Lens for Myopia 7 to -19 Diopters," Journal of Refractive Surgery, 1998, vol. 14 (3), pp. 282-292.

CILCO advertisement brochure, Oct. 1982, 3 pages.

International Preliminary Report on Patentability for Application No. PCT/US08/061180, mailed on Oct. 27, 2009, 8 pages.

International Preliminary Report on Patentability for Application No. PCT/US2009/038469, mailed on Sep. 28, 2010, 10 pages.

International Search Report and Written opinion for Application No. PCT/US08/061180, mailed on Sep. 5, 2008, 10 pages.

International Search Report and Written opinion for Application No. PCT/US09/038469, mailed on Aug. 10, 2009, 12 pages.

Kim J.H., et al., "The Analysis of Predicted Capsular Bag Diameter using Modified Model of Capsule Measuring Ring in Asians," Clinical and Experimental Ophthalmology, 2008, vol. 36 (3), pp. 238-244.

Marinho, "Results are encouraging for phakic IOLs, but more work is needed," Ocular Surgery News, Refractive Surgery, pp. 12-15, 2000.

Menapace R., et al, "Capsular Tension Rings," Cataract and Refractive Surgery, 2008, pp. 27-44.

Strenn K., et al., "Capsular bag Shrinkage after Implantation of an Open-loop silicone lens and a Poly(methyl methacrylate) Capsule Tension Ring," Journal of Cataract and Refractive Surgery, 1997, vol. 23 (10), pp. 1543-1547.

Tehrani M., et al., "Capsule Measuring Ring to Predict Capsular Bag Diameter and Follow its Course after Foldable Intraocular Lens Implantation," Journal of Cataract Refractive Surgery, 2003, vol. 29 (11), pp. 2127-2134.

U.S. Appl. No. 12/412,338, filed Mar. 26, 2009.

Vass C., et al, "Prediction of Pseudophakic Capsular bag Diameter based on Biometric Variables," Journal of Cataract and Refractive Surgery, 1999, vol. 25 (10), pp. 1376-1381.

WO 01/54569 Machine Translation. Manfred Tetz and Stephan Schruender. May 12, 2000.

ANGLE INDICATOR FOR OCULAR MEASUREMENTS

RELATED APPLICATIONS

The present application is a continuation of application U.S. Ser. No. 11/739,392 filed on Apr. 24, 2007, now U.S. Pat. No. 7,993,398 issued on Aug. 9, 2011, the entire contents of which are incorporated herein by reference.

BACKGROUND OF THE INVENTION

1. Field of the Invention

The present invention is directed to methods and devices for making and using ocular measurements, more particular for making and using ocular measurements of a cavity size within an eye such as the capsular bag of a human eye.

2. Description of the Related Art

Recently, a great deal of effort has been devoted to developing an accommodating intraocular lens, which can adjust its power over a particular range to clearly view both near and far objects. The accommodating intraocular lens is generally inserted into the capsular bag of the eye, which is a transparent structure that houses the natural lens of the eye and generally remains in the eye after the natural lens has been surgically removed.

The accommodating intraocular lens changes its power in response to a squeezing and/or expanding force applied to the lens by the capsular bag via the ciliary muscle.

It is generally important to know the size (or more precisely, the inner diameter or circumference) of the capsular bag for each patient's eye, prior to insertion of the intraocular lens. The capsular bag size may vary patient-to-patient or eye-to-eye, and if the bag is larger or smaller than expected, the lens may end up slightly expanded or squeezed upon implantation. This, in turn, may result in a shift in the nominal base power and/or a reduction in the accommodation range, both of which are undesirable.

Although the capsular bag diameter is a desirable and useful quantity, it is also quite difficult to measure.

There have been attempts to measure the capsular bag size with ultrasound. While ultrasound may be useful for determining the central thickness of the unoperated lens, it is not generally versatile enough to image the entire crystalline lens, and cannot reliably read out to the perimeter of the lens.

There have been attempts to measure the capsular bag by inserting a capsular tension ring (CTR) into the eye. See, for instance, K. STRENN, R. MENAPACE, and C. VASS, "Capsular bag shrinkage after implantation of an open-loop silicone lens and a poly(methyl methacrylate) capsule tension ring," J Cataract Refract Surg, 1997, pp. 1543-1547, Vol. 23, which is hereby incorporated by reference in its entirety. In this reference, a CTR indicates the capsular diameter, based on linear measurement of a peripheral gap. After the measurement, the CTR is generally not removed from the eye and remains resident in the eye, which may be undesirable.

There have been attempts to correlate capsular bag size with other eye properties that can be measured more easily. See, for instance, C. VASS, R. MENAPACE, K. SCHMETTERER, O. FINDL, G. RAINER AND I. STEINECK, "Prediction of pseudophakic capsular bag diameter based on biometric variables," J Cataract Refract Surg, October 1999, pp. 1376-1381, Vol. 25, which is hereby incorporated by reference in its entirety. In this reference, measurements of capsular bag diameter were taken on a sample of patients, using the CTR noted above. In addition, measurements of corneal power and axial length were taken on the same patients, using known methods. A regression analysis of the measurements produced a statistically significant correlation between capsular bag diameter and corneal power and axial length, but not with a sufficient accuracy for predicting the required size of an accommodating intraocular lens.

There have been attempts to convert the capsular bag circumference dimension to a linear dimension, then to measure the linear dimension with a camera or visually. See, for instance, M. TEHRANI, H. B. DICK, F. KRUMMENAUER, G. PFIRRMANN, T. BOYLE and B. STOFFELNS, "Capsule measuring ring to predict capsular bag diameter and follow its course after foldable intraocular lens implantation," J Cataract Refract Surg, November 2003, pp. 2127-2134, Vol. 29, which is hereby incorporated by reference in its entirety. In this reference, a Koch capsule measuring ring is inserted into the eye. The ring is an incomplete circle, with appendices on each end, so that when the ring is inserted into the capsular bag, the separation between the appendices is related to the capsular bag circumference. The ring is left in the eye after the measurement is taken, which may be undesirable.

In addition, for the above reference, the measurement of the appendix separation may be disadvantageous for two reasons. First, the measurement is taken at the peripheral edge of the eye, which is a difficult region of the eye for measurement. For instance, the region to be measured might be outside the area of the pupil, and might require use of a slitlamp, or unusual and undesirable handling of the pupil. Second, it is difficult to measure a linear dimension in the eye. Often, such a measurement is taken through the cornea, which can magnify the linear dimension, especially at the periphery of the eye. Because corneal powers may vary from patient-to-patient and eye-to-eye, there may be a significant uncertainty in any linear measurements taken through the cornea. In addition, because most eye surgery is performed through a microscope, the measurement may have to be taken through the microscope, which may have a zoom feature or a variable focal length that may further complicate a linear dimension measurement.

Accordingly, there exists a need for an apparatus and method for measuring the size of the capsular bag of an eye, which does not rely on a linear measurement at the periphery of the eye.

DETAILED DESCRIPTION OF THE DRAWINGS

Implantation of an intraocular lens in an eye may require the accurate measurement of the size (e.g., circumference or the diameter) or position of the capsular bag of the eye. After the natural crystalline lens has been surgically removed, a flexible sizing ring may be inserted into the capsular bag for measuring the size, diameter, or circumference of the capsular bag, or for determining the position of the capsular bag, for example, relative to the pupil of the eye. The ring compresses to fit through a surgical incision, then expands to fill the capsular bag along an equatorial region via resiliency of the ring and/or manipulation by the practitioner inserting the ring. The ring has a central component that changes shape as the ring is compressed, where a relatively small change in circumference produces a relatively large change in shape. The shape may be measured visually or with a camera through the cornea, and is independent, or at least substantially independent, of corneal or camera magnification. The ring extends into the center of the capsular bag and is compliant, so that it may be safely removed by grasping the central features and withdrawing it from the capsular bag. While the sizing ring may be used in conjunction with any intraocular lens or similar device to be placed within a capsular bag, the ring may be particularly useful when used with accommodating intraocular lenses, where function of the intraocular lens may be particularly sensitive to fit inside the capsular bag. Additionally or alternatively, the ring may be used for sizing other portions of the eye such as the sulcus or anterior chamber of the eye.

Figure 1:
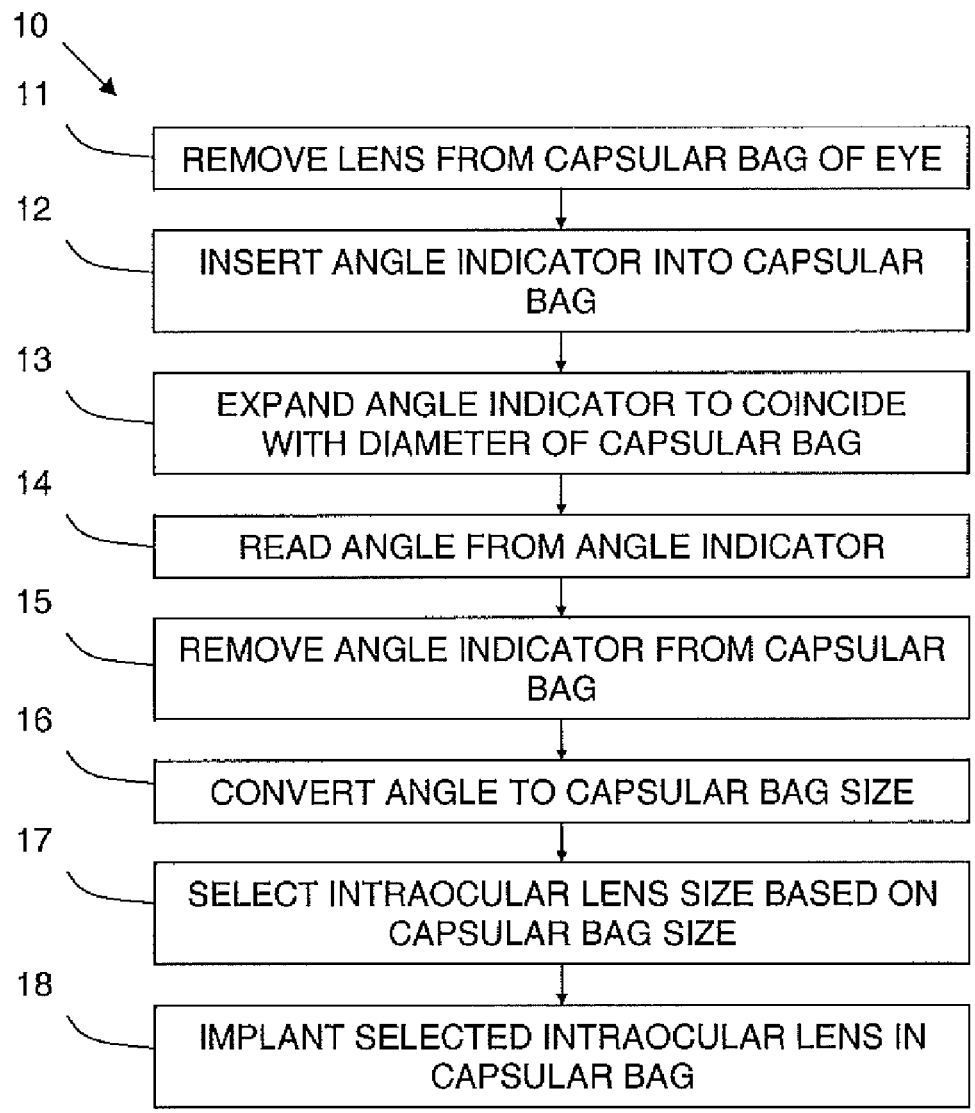
FIG. 1 is a flow chart of a method of replacing a lens in the capsular bag of an eye.

FIG. 1 is a flow chart of an exemplary method 10 of replacing a lens in the capsular bag of an eye.

In element 11, the lens is removed from the capsular bag of the eye. The removed lens may be the natural crystalline lens of the eye, which has become opaque due to cataracts, or has become damaged by some other disease or injury. Alternatively, the removed lens may be an existing intraocular lens. Typically, the lens is removed in a surgical procedure in which the lens is broken up and vacuumed out of the eye. The capsular bag, which supports the lens before removal, is retained in the eye, and may be used to support a replacement lens.

The replacement lens may be an intraocular lens, such as an accommodating intraocular lens, which relies on forces transferred by the zonular fibers in the eye to the capsular bag. These forces can change the power and/or location of the lens by distorting and/or translating one or both of the lens surfaces. The distorting force exerted by the zonular fibers is limited by the finite strength of the lens capsule, fibers, and surrounding structures, and typically the intraocular lenses are designed to use this limited force to change power to cover all or part of the range of accommodation for the eye. As a result, the intraocular lens may be quite sensitive to compressive or expansive forces applied to its equator, and may be designed to work optimally for a particular size of capsular bag. If the patient's capsular bag is larger or smaller than expected, the intraocular lens may experience a shift in nominal power, or a truncation of the accommodation range, which may be undesirable. Accordingly, it may be useful during a surgical procedure to measure the actual size of the capsular bag, so that an intraocular lens may be selected for implantation that corresponds to the actual size of the capsular bag.

In element 12, an angle indicator is inserted into the capsular bag. During insertion, it is often desirable to use as small an incision as possible, so the angle indicator may optionally be inserted in a folded state.

In element 13, the angle indicator is expanded to coincide with a diameter of the capsular bag. If the angle indicator is inserted in a folded state, it may be first unfolded to reach its full size. The capsular bag material is flexible, so that it may be bent and reshaped. It may be relatively straightforward to position the angle indicator, which is generally ring-shaped, along the equator of the capsular bag. Typically, some gentle, back-and-forth motions applied by the surgeon are sufficient to move the angle indicator to lie along the equator of the capsular bag. In general, the shape of the empty capsular bag is such that it may be well-approximated as circular when viewed from the front. Any azimuthal errors in the positioning of the angle indicator do not significantly affect the angular reading from the angle indicator, or the measured value for the capsular bag size.

In element 14, once the angle indicator is aligned along the equator of the capsular bag, the angle is read from the angle indicator. The angle may be formed from the intersection of two generally straight elements on the angle indicator. In some embodiments, the intersection is substantially centrally disposed within the pupil of an eye into which it has been placed, for example, to aid in measuring the angle thus formed. Alternatively, the straight elements may be relatively long (e.g., to provide a predetermined sensitivity), wherein the intersection between the two generally straight elements may be near the edge of the pupil or outside the pupil. The angle may be seen visually by the surgeon or by a camera or microscope trained on the eye. Alternatively or additionally, the angle may be determined by producing an electronic or digital image of the angle indicator and processing the image using software or algorithms known in the art.

In element 15, once the angle has been read, the angle indicator may be removed from the capsular bag of the eye. The angle indicator may be folded upon itself for removal, which is especially convenient if the angle indicator is inserted in the folded state. Alternatively, the angle indicator may be broken or separated into segments, and then the segment may be removed through the incision in the eye. In one embodiment, the angle indicator includes cutaways on its posterior surface, or other location, which may allow sectioning in vivo for removal of the angle indicator.

In element 16, once element 14 has been performed and the angle is read from the angle indicator, the read angle is converted to a capsular bag size. The size may be reported as a diameter, or, equivalently, as a circumference. The conversion may be done by reading values off a printed table, by reading values off a graph, by plugging the read angle into a predictive formula, by a computer, or directly by comparing the angle to a dedicated device. Alternatively or additionally, the location of the capsular bag may be determined within the eye, for example, relative to the location of the pupil or the macula.

In element 17, once element 16 has produced a value of the capsular bag size, an intraocular lens may be selected. The lens selection may be based in part on the capsular bag size, as well as on other data, such as the required lens power, an available amount of accommodative force, and/or a targeted range of accommodation.

For instance, for a given required nominal lens power, there may be several intraocular lenses available, each sized for a particular capsular bag diameter. The available lenses may be part of a kit, with diameter spacings of 0.5 mm, 0.25 mm, 0.2 mm, 0.15 mm, 0.1 mm, 0.05 mm, or any suitable value. Typically, the exact size value given from element 16 may not be exactly available in the kit, and the surgeon or practitioner may have to round off to the nearest size that is available in the kit.

Alternatively, the intraocular lens may have an adapter that can attach to the circumference of the lens, which allows a single lens to be used with multiple sizes of capsular bags.

As a further alternative, the intraocular lens may itself be adjustable, for instance, with an adjustable haptic that can couple a particular optic to a capsular bag sized within a particular range.

In element 18, once an intraocular lens is selected from element 17, the selected lens may be surgically implanted in the capsular bag.

Note that element 15 follows element 14, and elements 16 and 17 follow element 14, but elements 16 and 17 need not follow element 15. For instance, element 15 may follow element 17, which follows element 16, which follows element 14. The conversion of the read angle to a capsular bag size and the selection of a lens based on the capsular bag size are essentially independent of removal of the angle indicator from the capsular bag, and these elements may be performed in any suitable order.

Figure 2:
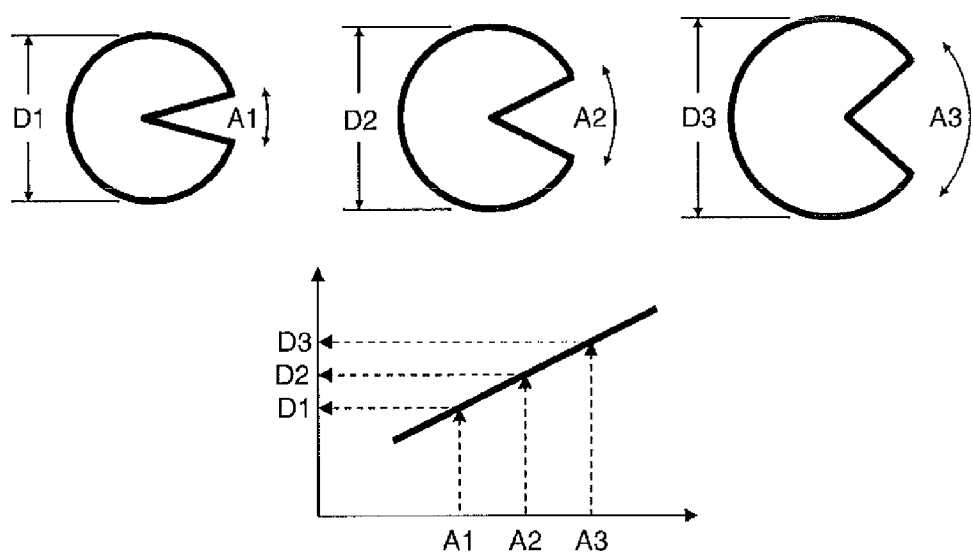
FIG. 2 is a schematic drawing of an angle indicator at three exemplary capsular bag sizes.

A schematic drawing of the angle indicator itself is shown in FIG. 2. The angle indicator is shaped roughly like a broken ring, with the broken portion of the ring replaced by two segments that connect near the center of the ring. The ring is inserted into the capsular bag and expands until it is coincident with a diameter of the capsular bag. As the ring itself expands and contracts, the angle between the two segments increases and decreases.

The ring may be designed so that a relatively small change in diameter produces a relatively large change in angle. For instance, three exemplary diameters D1, D2 and D3, are shown in FIG. 2, along with their corresponding angles A1, A2 and A3. The relationship between measured angle and ring (and, therefore, capsular bag) diameter is shown in the exemplary plot in FIG. 2. Note that the relationship need not be truly linear, as shown in FIG. 2, but may have any suitable increasing relationship, such as a quadratic or more complex polynomial relationship. During use, the practitioner inserts the angle indicator into the capsular bag, expands the angle indicator to fill the capsular bag, reads the angular value from angle indicator, and converts the read angular value to a capsular bag diameter, or equivalently, circumference.

Note that the angle is viewable near the center of the pupil of the lens, rather than only at the edge of the pupil or the edge of the capsular bag. This reduces the need for unusual viewing techniques, or extra handling of the pupil, and may help reduce distortion of the angle when viewed through the patient's cornea.

In one embodiment, the angle indicator remains substantially round, for all angles/diameters within a particular range. This is accomplished by varying the radial thickness of the ring, with a maximum thickness opposite the two segments, and a minimum thickness in the regions adjacent to the joints that attach the straight segments to the rest of the ring. This is shown more clearly in FIG. 3.

Figure 3:
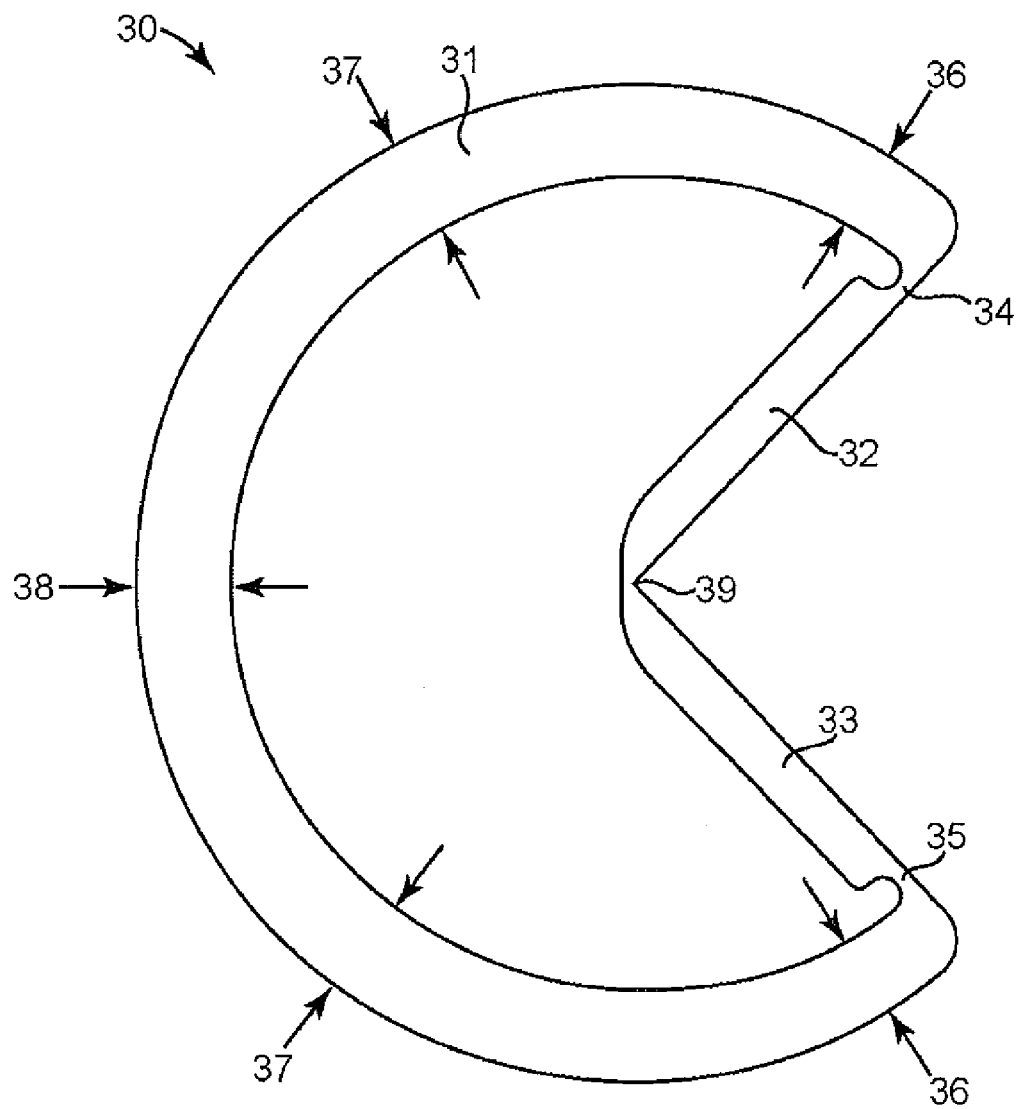
FIG. 3 is a front-view plan drawing of the angle indicator of FIG. 2.

FIG. 3 is a front-view plan drawing of an angle indicator 30. An incomplete annulus 31, shaped generally as an open-ended ring-shaped portion, is hingedly connected to two straight sections 32 and 33 that are hingedly connected to each other in the interior of the circle.

The incomplete annulus 31 may optionally have a varying radial thickness around its circumference. Adjacent to the hinges 34 and 35, the radial thickness 36 may be its minimum. The radial thickness may increase farther away from the hinges 34 and 35, reaching an intermediate value 37 partially around the ring, and may finally reach a maximum value 38 directly opposite and between the hinges 34 and 35. Alternatively, the radial thickness may be constant around its circumference, or may vary in a manner other than the exemplary manner described above.

In the exemplary design of FIG. 3, the out-of-plane thickness is essentially constant along the incomplete annulus 31 and segments 32 and 33. The corners may be rounded, or may be un-rounded.

The variation in radial thickness around the ring helps ensure that the incomplete annulus stays essentially round, even as the angle between the straight segments 32 and 33 varies. As such, the diameter dimensions D1, D2 and D3 in FIG. 2 are truly diameters, and the outermost shapes of the angle indicators are essentially round at each of the three sizes shown. The angle indicator 30 retains its round periphery as it is compressed.

Alternatively, the radial thickness of the angle indicator 30 may remain essentially constant around the ring, and the out-of-plane thickness may vary along the ring. As a further alternative, both the radial thickness and the out-of-plane thickness may vary around the ring.

The hinges 34 and 35 may be formed integrally as weakened portions of the angle indicator 30. In one embodiment, the hinges 34 and 35 are formed at regions of reduced in-plane thickness at the intersections of the straight segments 32 and 33 with the incomplete annulus 31. As such, the hinges 34 and 35 may bend freely in the in-plane direction, allowing the angle indicator to freely expand and contract to attain its maximum size inside the capsular bag. The hinges 34 and 35 may be configured to preclude or reduce movement of the two segments 32 and 33 out of the plane of the angle indicator 30.

The segments 32 and 33 are joined to each other by a third hinge 39, which is also formed as a reduction in the in-plane thickness near the hinge, also permits free in-plane movement of the segments with respect to each other and free diametric expansion and compression of the angle indicator 30, and also restricts out-of-plane movement.

Note that the segments 32 and 33 are shown in the figures as being entirely straight. In practice, there may be some curvature to all or a portion of either or both of the segments. For instance, there may be some local waviness to all or a portion of the segments 32 and 33. Alternatively, there may be a more global curvature, having a radius on the order of or larger than the angle indicator radius. In one embodiment of the angle indicator, the segments 32 and 33 are straight throughout.

Note that the angle indicator 30 may measure capsular bags having a size larger than the incision through which the angle indicator is inserted. For instance, the angle indicator may measure capsular bag diameters on the order of 11 mm. In general, the diameter of the angle indicator in an uncompressed state is at least about 9 millimeters in diameter, but may be between about 8 millimeters and about 15 millimeters, preferably between about 9 millimeters and about 12 (nominal to date is 11-jd) millimeters. As such, the angle indicator 30 may be compressed in an injector or folded upon itself during insertion (and later, during extraction), and may be unfolded and expanded for performing the measurement. When used in conjunction with an accommodating intraocular lens, the angle indicator is configured to fit through an incision in the eye that is less than about 5 millimeters, preferably less than 4 millimeters. In other embodiments, for example when used with an intraocular lens that does not provide accommodation, the angle indicator is configured to fit through an incision in the eye that is less than about 3 millimeters, preferably less than 2 millimeters.

During insertion and positioning of the angle indicator 30, it may be beneficial to gently "force open" the straight segments 32 and 33 of the angle indicator 30. This may be accomplished by applying a force on or near the rear (essentially flat) side of the hinge 39, directed outward from the ring, toward the opening between the segments. The force may be applied by the practitioner using the equipment that is typically used to position objects during surgery, such as a hook or forceps. Because the force may be applied directly to angle indicator 30, there may be no need for extra holes or tabs for this purpose, although holes and/or tabs may optionally be used.

In certain embodiments, the angle indicator 30 is configured to produce a relatively small force when placed within a capsular bag. For example, the force produced by the angle indicator 30 when the diameter is compressed 2 millimeters may be between about 0.5 gram and about 20 grams, preferably between about 0.5 gram and 5 grams. Such low forces may beneficially reduce the possibility of damaging the capsular bag during use of the angle indicator 30, but may require manipulation by the practitioner to insure that the incomplete annulus 31 fully engages the equatorial region of the capsular bag. Alternatively, a higher force may be used to ensure positive engagement of the equatorial region of the capsular bag with a minimal amount of adjustment by a practitioner, for example, a force of between about 10 grams and about 30 grams or more.

The length of the segments 32 and 33 may be varied, so that the hinge that joins them may fall on either side of the center of the ring at its nominal position. As the segment length is increased, the angle becomes easier for the practitioner to read during use, although the sensitivity is decreased. Likewise, as the segment length is decreased, the angle becomes more difficult for the practitioner to read during use, but the sensitivity is increased. In practice, the designer of ordinary skill in the art understands this trade-off, and may design an angle indicator 30 with a suitable range of operation, a suitable sensitivity, and a suitable ease of angle viewing.

Optionally, there may be more than one angle indicator for a particular eye or patient, with each angle indicator covering a particular range of capsular bag sizes. For instance, one angle indicator may be used for capsular bag diameters in the range of 9 to 10 mm, and another angle indicator may be used for the range 10 to 11 mm. These values are merely exemplary, and any suitable ranges may be used.

Note that because the angle may be measured from roughly the center of the pupil, there is generally little distortion of the angle caused by the cornea. If the cornea imparts a magnification an image of the segments forming the angle, the segments themselves may appear to grow or shrink in size, but the angle between the segments remains essentially unchanged. This holds for a wide range of cornea radii, and a wide range of magnifications caused by the cornea.

It is instructive to perform some trigonometry to more accurately show the graphical dependence of measured angle A and capsular bag diameter D, which is not truly linear as shown schematically in FIG. 2, but has a more complicated dependence.

Figure 4:
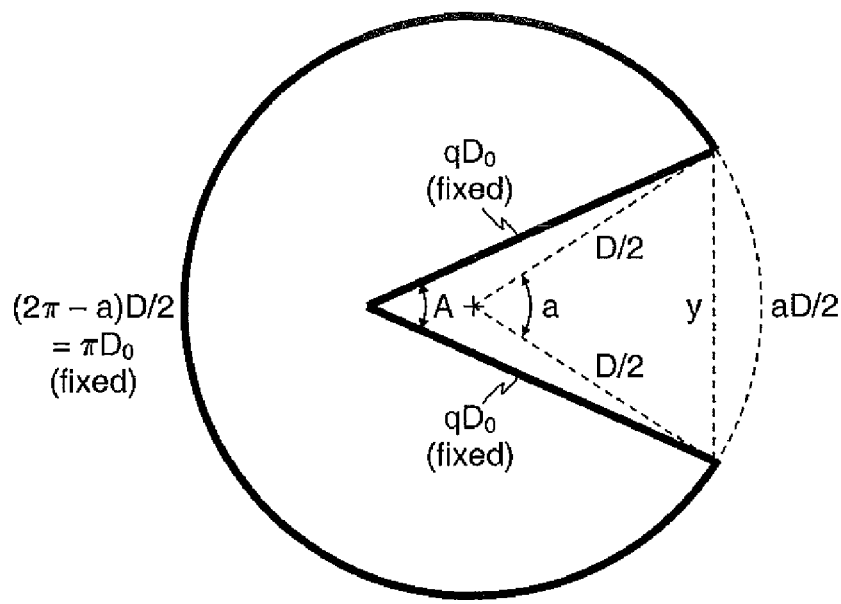
FIG. 4 is a schematic drawing of an approximate geometry of the angle indicator of FIGS. 2 and 3.

FIG. 4 shows an exemplary geometry for one embodiment of an angle indicator. We assume for this simplistic analysis that the lengths of the incomplete annulus (i.e., the open ring-shaped segment) and the straight segments remain constant during use; this is a good approximation for this purpose.

Both the length of the incomplete annulus and the length of each straight segment may be related to a "closed diameter" $D_0$, which is the diameter of the angle indicator when the segments are parallel, or "closed". The length of the incomplete annulus is $\pi D_0$, and the length of each straight segment is $qD_0$, where q is a dimensionless quantity than can between 0 and 1. When q is 0.5, the straight segments extend to exactly the center of the ring when the ring is "closed". When q is 1, the straight segments extend all the way to the opposite end of the ring when the ring is "closed". When q is 0, the straight segments are infinitesimally small.

During use, the angle indicator expands to a diameter of D, with a measured angle A between the straight segments. Length y and angle a are mathematical constructs. We attempt to solve for A in terms of D.

First, solve for y: $y = D \sin(a/2)$.

Next, we express angle a in terms of the length $\pi D_0$ of the incomplete annulus: $a = (2\pi - 2\pi D_0/D)$.

Plug into expression for y: $y = D \sin(\pi - \pi D_0/D) = D \sin(\pi D_0/D)$

Can also solve for y in terms of a and $qD_0$: $y = 2qD_0 \sin(A/2)$

Figure 5:
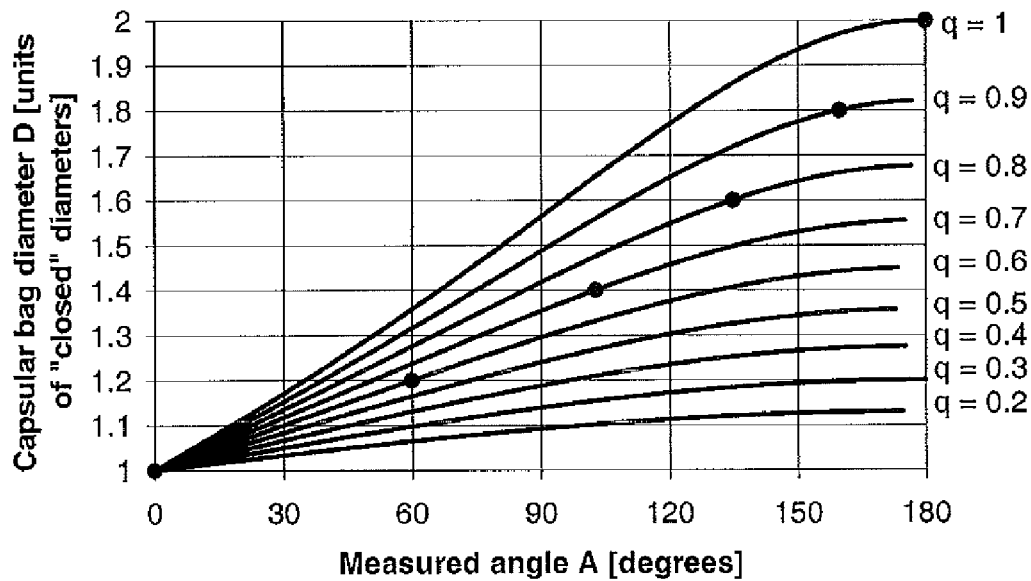
FIG. 5 is a plot of capsular bag diameter versus measured angle a, for a variety of straight segment lengths, for the approximate geometry of FIG. 4.

Set these two expressions for y equal to each other and rearrange to get: $\sin(A/2) = \sin(\pi D_0/D)/(2qD_0/D)$ Solve for A and rewrite as $A = 2 \sin^{-1}([\pi/2q] \times [\sin(\pi D_0/D)/(\pi D_0/D)])$ FIG. 5 is a graph of the above equation, which predicts capsular bag diameter D versus measured angle A, for several values of q.

The choice of q is related to both sensitivity and dynamic range. For relatively short straight segments (low q), there is high sensitivity and low dynamic range. Similarly, for relatively long straight segments (high q), there is low sensitivity and high dynamic range.

In some embodiments, it is preferable if the vertex, or intersection between the straight segments, is located at or near the center of the ring for at least part of the range of use. The circles superimposed on the various plotted curves in FIG. 5 show the operating condition at which the vertex is at the center of the ring. Note that for short segments (q<0.5), there is no condition under which the vertex can be located in the center of the ring; these segments are just too short to extend to the center, regardless of angle A.

Note that for q=0.6 (i.e., where the straight segments are 20% longer than the radius of the "closed" ring), the vertex falls at the center of the ring at a measured angle A of 60 degrees. In one embodiment, this may be a preferable set of conditions; the plotted region for q=0.6 is enlarged and is shown in FIG. 6.

Figure 6:
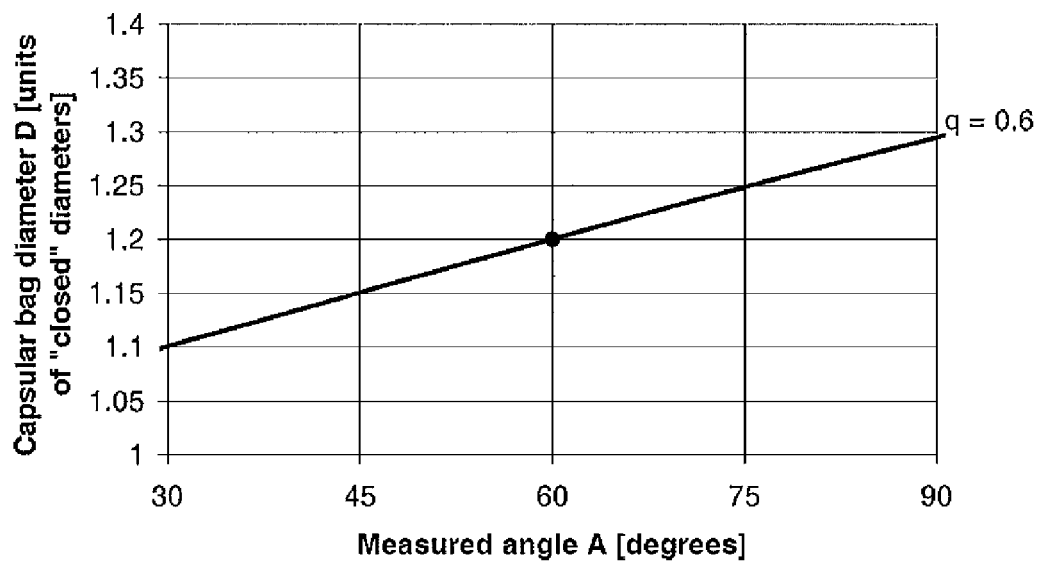
FIG. 6 is a close-up of the q=0.6 plot of FIG. 5.

For FIG. 6, we choose a convenient set of numbers, which are merely exemplary and are not intended to be limiting in any way. For instance, if we wish to measure capsular bags having a diameter in the range of 11 mm to 13 mm, we use an angle indicator having a "closed" diameter of 10 mm and a short segment length of 6 mm, and detect angles between 30 and 90 degrees. If our detection scheme allows us to detect angle A to the nearest 15 degrees, we may measure the diameter of the capsular bag to the nearest 0.5 mm (based on the 10 mm diameter of the angle indicator). These values are merely exemplary, and any lengths and diameters may be scaled upwards or downwards. Other suitable values may also be used.

Note also that the mathematical analysis that generates the plots of FIGS. 5 and 6 is approximate, and assumes that the lengths of the ring-shaped segments and the two straight segments all remain constant throughout operation. This is only an approximation, and one of ordinary skill in the art will readily appreciate that more sophisticated simulations may be performed that account for local stresses and deformations, bending of the materials, and other effects not considered in the simplistic analysis presented above.

The discussion thus far has focused primarily on the angle indicator, which generates an angle as a function of the capsular bag size. The following paragraphs focus primarily on an exemplary protractor for reading the angle generated by the angle indicator.

Once the angle indicator is inserted into the capsular bag and expanded to its fullest extent, the straight segments form an angle that is visible through the cornea. The angle may be viewed by eye, or may be viewed through a microscope, camera, or any suitable imaging system. Because the angle may be subject to distortion by a camera or imaging system, one angle measurement embodiment is a protractor that may be removably placed on the cornea.

For the purposes of this document, the term "protractor" may include any instrument or device that can read an angle visually or by electronic means. For instance, a protractor may include a flexible sheet (e.g., a contact lens) having radial marks, a circular device having regular markings at predetermined locations along its circumference, and so forth. A protractor may also include software that can return a measured angle value for an angle embedded within an image. Additionally, a protractor may include a calibrated reticle for an optical instrument, such as a microscope or a camera. The increments on the protractor may include one half degree, one degree, five degrees, 10 degrees, 15 degrees, 20 degrees, 25 degrees, 30 degrees, 35 degrees, 40 degrees, 45 degrees, or any suitable increment. Alternatively, the protractor may be marked with indicia that correspond directly to the capsular bag size or appropriate ranges corresponding to available implant sizes.

Figure 7:
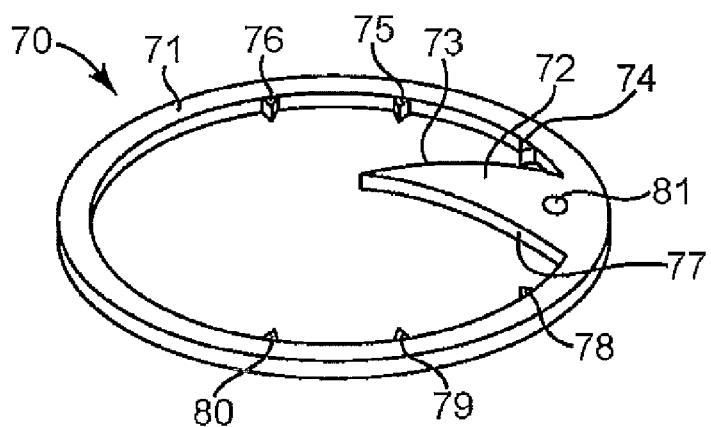
FIG. 7 is an isometric drawing of a protractor.
Figure 8:
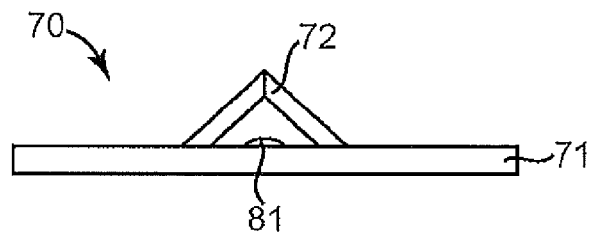
FIG. 8 is a plan drawing of the protractor of FIG. 7.
Figure 8:
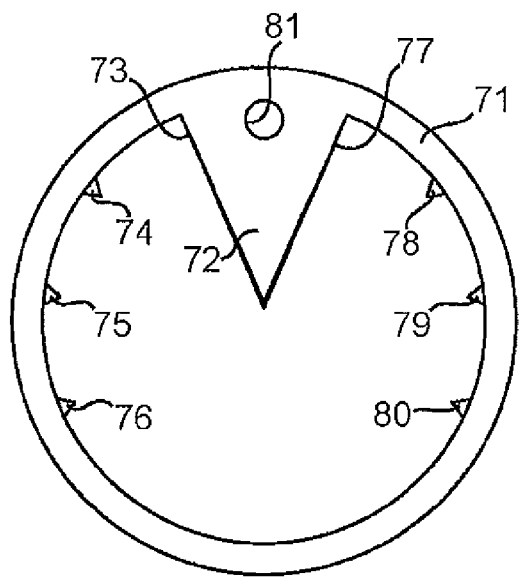
Figure 8:
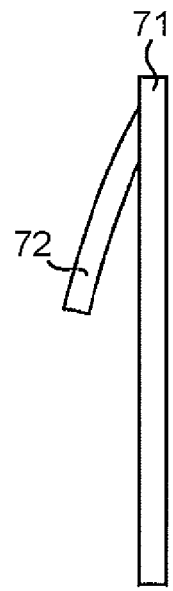

An exemplary protractor 70 is shown in the isometric drawing of FIG. 7 and the three views of the plan drawing of FIG. 8.

The protractor 70 has a generally circular ring 71 that is sized to rest on the cornea to allow measurement of the angle from the angle indicator. The ring 71 is small enough to fit on the eye of the patient, and large enough to surround the pupil of the eye. A typical range of diameters for the protractor ring may be from about 3 mm to about 12 mm, or from about 5 mm to about 8 mm.

Note that the straight segments 32 and 33 of the angle indicator 30 are viewable from roughly the center of the pupil, rather than requiring a measurement taken at the edge of the capsular bag. As a result, ring 71 of the protractor need not extend all the way to the edge of the capsular bag or to the edge of the cornea. The ring 71 may optionally have rounded or chamfered edges that may reduce the risk of scratching the cornea.

The protractor 70 has a reference portion 72 that has radial edges 73 and 77. During use, the reference portion 72 generally extends out of the plane of the ring 71, so that it may rest upon or extend over the cornea, which is curved. When viewed from the front, the intersection of radial edges 73 and 77 may fall at or near the center of the ring 71, and/or at the intersection of the straight segments 32 and 33 (e.g., at the hinge 39). Note that the reference portion 72 may deform so that this intersection of radial edges 73 and 77 may lie away from the center when the protractor is not in use.

In one embodiment, the protractor is rigid, so that the protractor roughly maintains its shape before, during and after use. In this embodiment, the reference portion 72 may extend out of the plane of the ring 71 in its relaxed state before use. Alternatively, the reference portion may 72 may be located roughly in the plane of the ring 71 before use, and may pivot in the anterior direction during use. The pivoting may occur around a weakened portion of the reference portion, which may include an optional hole or void area 81. In some embodiments, the void area 81 may have a more complex shape that the hole shown in FIG. 7, for example, to provided a weakened zone with predetermined bending characteristics or to avoid confusion that the void area 81 represents an alignment mark with the straight segments 32 and 33.

In another embodiment, the protractor 70 is flexible, and may be draped onto the cornea of the eye. Such a flexible protractor conforms generally to the shape of the cornea, without significantly deforming in the plane of the protractor. The protractor 70 may be made from a largely transparent material, and may include markings or features that indicate predetermined angle values. For instance, the protractor 70 may include a central feature that may be overlaid with the hinge 39 during use, and various angular features, such as reticle marks or other radial lines or features. In one embodiment of a flexible protractor 70, the protractor may be formed on or be made integral with a contact lens that is placed onto the cornea during use.

For the protractor 70 of FIG. 7, the protractor is positioned during use so that one of the radial edges 73 and 77 lines up with one of the straight segments 32 and 33. The other straight segment falls elsewhere around the circumference of the ring, and may fall near one of several calibration features, such as notches, tabs, holes, extensions, annotations, colors or members.

For instance, if radial edge 73 is aligned with straight segment 32, then straight segment 33 may fall near one of feature 74, feature 75 or feature 76. The features may be in calibrated increments, such as 30 degrees, 20 degrees, 15 degrees, 10 degrees, 5 degrees, 1 degree or less, or any suitable increment. For instance, if the increment is 30 degrees between each of the features 74-76, then if the straight segment 32 falls closest to the feature 74, then the angle of the indicator is closest to 30 degrees. Similarly, if the straight segment 32 falls closest to the feature 76, then the angle of the indicator is closest to 90 degrees.

In addition, there is a second set of radial edge 77 and features 78-80, which may be used equally as well as the first set of radial edge 73 and features 74-76. The second set may be calibrated with the same angular increment as the first, or with a different angular increment as the first.

Alternatively, there may be more than three or fewer than three features. In addition, the features may be evenly or unevenly spaced.

Once the measurement has been taken, the protractor 70 may be removed from the cornea of the patient. In one embodiment, the protractor 70 may be removed by grasping it with the hole 81, or by an optional elevated feature or tab (not shown).

There may be other suitable angular measurement devices that may be used, as alternatives to the device shown in FIGS. 7 and 8. For instance, a more conventional protractor may be used, with notches, tick marks, lines, or other visual cues extending around the circumference at a prescribed interval, such as every 30 degrees, or any other suitable interval. This more conventional protractor may lack the reference portion 72. As another example, the protractor may be made from a soft material that is draped over the cornea or rests on the facial tissue that surrounds the eye, rather than on the eye itself. Alternatively, the angle may be measured from an image formed of the eye on a screen or in software. As a further alternative, there may be an angular reticle supplied with a camera or microscope, which may allow a reading of the angle.

The angle indicator 30 may be made integrally as a single unit, or may be made from several pieces that are assembled. The assembled pieces may be made from the same or from different materials.

Both the angle indicator 30 and the protractor 70 may be made from any suitable biocompatible and flexible materials. For instance, either or both may be made from silicone or any polymeric material, PMMA, or any other suitable material. In one embodiment, the material or materials used may be moldable, and may not be hydrophilic. In one embodiment, the material is sterilizable by autoclave, by ETO, or by any suitable sterilization process. The angle indicator 30 and protractor 70 may be made from the same or from different materials. The angle indicator 30 and protractor 70 may be made of a tinted, opaque or fluorescing material, so that they may easily be read visually.

In one embodiment, the angle indicator and protractor may be supplied in pre-sterilized, sealed packages that accompany an intraocular lens. Both the angle indicator and protractor may be unsealed when needed, and disposed of once a measurement has been taken.

In one embodiment, there may be sets of angle indicators and protractors, with each set corresponding to a different range of capsular bag sizes. For instance, one set may be used for a size range of 9 to 10 mm, and another set may be used for a size range of 10 to 11 mm. Each set may be color-coded so that the particular protractor is easily associated with its corresponding angle indicator, and the measured angles are easily associated with their proper measured capsular bag sizes. Alternatively, there may be other identifying characteristics for matched sets of angle indicators and protractors, such as texture, etching, surface characteristics, ridges and so forth.

In certain embodiments, an electronic or digital image of the angle indicator 30 in the eye and/or the protractor 70 is produced. The digital image may be captured and processed using a computer or other electronic system in order to determine the angle between the two straight sections 32 and 33. The resulting digital representation may be used to increase the accuracy of the angle measurement, as a cross-check to a manual measurement, or to provide other information (e.g., the location of the angle indicator and/or capsular bag within the eye, or to determine a change in size of the capsular bag, as discussed in greater detail below).

In one embodiment, the outer edges of the angle indicator may expand through viscoelastic/OVD in the capsular bag.

In one embodiment, the straight segments, or central arms, of the angle indicator may extend past the center of the angle indicator. These longer straight segments may fill a larger area of the pupil, and may provide an easier measurement than smaller or shorter straight segments.

In one embodiment, the angle indicator may be inserted into the capsular bag by an injector.

In one embodiment, the angle indicator may include a tether, so that the angle indicator may be more easily withdrawn after the measurement has been taken. The withdrawing may be done directly by the tether. Alternatively, the tether may attach the angle indicator to an injector, so that the withdrawal may be done by the via injector.

In one embodiment, the angle indicator may include one or more loops on the straight segments or on the incomplete annulus that extend in the anterior direction (i.e., away from the patient's eye), for positioning and removal of the angle indicator.

In one embodiment, the flexural characteristics of the straight segments, or arms, their bases, and/or the central hinge may be "tuned" in shape or stiffness, so that the angle indicator may stay round over a wide range of compression.

In certain embodiments, the angle indicator 30 is made of a silicone material having a hardness of between about 70 durometer and about 80 durometer which approximately corresponds to a modulus of elasticity that may provide a desired compressive force when the angle indicator is placed within a capsular bag. In other embodiments, the modulus of elasticity of the angle indicator material (e.g., silicone or acrylic) and/or the width of the various angle indicator sections may be varied, so that reliable measurements may be made without excessively stretching the capsular bag.

In certain embodiments, the angle indicator 30 may be used to determine or estimate the resiliency of the capsular bag into which it is implanted. For example, the angle indicator 30 may be made of a material having a relatively high modulus of elasticity and/or may be otherwise configured to be relatively resilient or stiff. In some embodiments, two or more angle indicators 30 may be used. For example, a first angle indicator 30' may be inserted into the capsular bag that produces a relatively low force on the capsular bag (e.g., between about 0.1 gram to about 10 grams of force). As such, the first angle indicator 30' may be used to determine the size of the capsular bag when in a substantially unstressed state, as described in greater detail above. The first angle indicator 30' may then be removed from the eye and replaced by a second angle indicator 30" that is stiffer than the first angle indicator 30', thus producing a higher, radially outward force (e.g., in the range of about 5 grams to about 30 grams or more) when compressed by about the same amount as the first angle indicator 30'. Due to the increased force on the capsular bag, the bag is stretched by the second angle indicator 30" and thus produces a different bag size measurement. In some embodiments, the second angle indicator 30" additionally or alternatively has a diameter that is greater than the first angle indicator 30', thereby increasing the force produced on the capsular bag compared to that produced by the first angle indicator 30'. Other differences between the angle indicators 30', 30" may be advantageously used to provide a different radially outward force and/or to determine the resiliency of the capsular bag.

Alternatively, a single angle indicator 30 may be used that remains in the capsular bag; however, the size of the angle indicator 30 and/or on the capsule wall may be changed by increasing or decreasing the radially outward force of the incomplete annulus 31 or exerted on the incomplete annulus 31. The change in force may be produced by changing the resiliency of the angle indicator and/or by inserting another device or apparatus that applies additional force on the equatorial region of the capsular bag and/or angle indicator 30. In some embodiments, a surgeon may change the outward force on the incomplete annulus 31 by using one or more probes or other devices to push or pull at one or more locations on the incomplete annulus 31.

However the difference in size is induced, the resulting size difference may be measured and used to calculate a resiliency of the capsular bag and/or estimate the amount of accommodative force available for accommodation. In some embodiments, the change is size is quantitatively measured to determine a resiliency or other property of the capsular bag. Alternatively, the change in size may be qualitatively assessed so that the surgeon may broadly characterize a resiliency or other property of the capsular bag.

In certain embodiments, the angle indicator 30 is implanted within a capsular bag and the force produced by the ciliary muscle is changed in order to measure a change in the size and/or amount of force produced by the capsular bag. For example, a muscarinic agent such as a muscarinic agonist or a muscarinic antagonist may be used to alter the amount of accommodative force produced by the eye, as disclosed in U.S. Pat. No. 6,598,606 or US Patent Application Number 2005/0251254, which are herein incorporated by reference.

In one embodiment, the angle indicators are provided in a kit, with each angle indicator having a different expansile strength. Such a kit may be used to determine the elasticity of a particular evacuated capsular bag, in order to best determine the most compatible accommodating intraocular lens.

In one embodiment, the angle indicators are provided in a kit, with each angle indicator having a different axial thickness. Such a kit may help match the measurement of the capsular bag size to the axial thickness of the intended implanted intraocular lens, both at the edge of the lens and centrally.

In one embodiment, the central linear arms, or straight segments, include overlapping, curved vernier extensions. With reference to the exemplary design of FIG. 3, straight segment 32 may include one or more tangentially-curved extensions that protrudes toward segment 33, and straight segment 33 may also include one or more tangentially-curved extensions that protrudes toward segment 32, with the tangentially-curved extensions being located next to each other. In this manner, the angle may be read directly from the extensions, rather than with an additional external device such as a protractor.

In one embodiment, the incomplete annulus 31 may include extensions or tabs protruding from one or both of the straight segments 32, 33 and disposed along the circumference of, and in the plane of, the incomplete annulus 31. These optional extensions may help maintain the capsular circularity in the region between the straight segments 32, 33.

In addition to measuring the capsular bag size for intraocular lens implantation, the angle indicator, or variations thereof, may be used for other fields as well, such as measuring the diameters and stenosis of body cavities, especially in endoscopic and catheter-based procedures for sizing shunts and implants. The angle indicator allows estimation of a particular diameter, regardless of viewing magnification. This may also be used in the fields of interventional cardiology, as well as vascular, bariatric and gastroenteric surgeries. Furthermore, the angle indicator, or variations thereof, may also be used to measure the size of the anterior chamber or other cavities of the eye.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. An angle indicator for measuring the size of a capsular bag of an eye, comprising:
    a compressible, incomplete annulus having a first end, a second end, an interior, and an outer surface;
    a first segment attached to the first end of the incomplete annulus and extending into the interior of the incomplete annulus; and
    a second segment attached to both the second end of the incomplete annulus and a distal end of the first segment;
    wherein the first and second segments form an angle.

2. The angle indicator of claim 1,
    wherein the first segment is hingedly attached to the first end of the incomplete annulus; and
    wherein the second segment is hingedly attached to both the second end of the incomplete annulus and the first segment.

3. The angle indicator of claim 1, wherein the first segment comprises a first straight portion, and wherein the second segment comprises a second straight portion.

4. The angle indicator of claim 1, wherein the incomplete annulus has a varying radial thickness along its length, the radial thickness being greater at the midpoint between the first and second ends than at both the first and second ends.

5. The angle indicator of claim 1, wherein the angle formed by the first and second segments is acute.

6. The angle indicator of claim 1, wherein the incomplete annulus and the first and second segments are formed integrally.

7. The angle indicator of claim 1, wherein the incomplete annulus and the first and second segments are joined by hinges, each hinge comprising a reduction in in-plane thickness.

8. The angle indicator of claim 1, wherein the first and second segments have lengths greater than half the diameter of the incomplete annulus and less than the diameter of the incomplete annulus.

9. The angle indicator of claim 1, wherein the first and second segments have lengths equal to each other.

10. The angle indicator of claim 1, wherein the incomplete annulus and the first and second segments have rounded edges.

11. The angle indicator of claim 1, wherein the first and second segments are configured to form an angle visible through the pupil of an eye when the angle indicator is disposed in the capsular bag of the eye.

12. The apparatus of claim 11, wherein the annular portion has a diameter less than the diameter of a cornea of the eye.

13. An apparatus for measuring the size of a capsular bag of an eye, comprising:
    an angle indicator comprising an incomplete annulus and a pair of arms joined at an intersection therebetween, the arms disposed within the incomplete annulus, the joined arms operably coupled to first and second ends of the angle indicator and configured so that an angle formed by the arms varies in response to a diameter of a capsular bag of an eye; and
    a protractor for measuring the angle found by the arms.

14. The apparatus of claim 13, wherein each of the arms of the angle indicator comprises a straight portion.

15. The apparatus of claim 13, wherein the features of the protractor are at least one of protrusions, notches, and holes.

16. The apparatus of claim 13, wherein the features of the protractor are at least one of a color-code and an alphanumeric symbol.

17. The apparatus of claim 13, wherein the predetermined angular locations of the protractor are evenly spaced.

18. The apparatus of claim 13, wherein the protractor is flexible and is configured to be draped over a cornea of the eye.

19. The apparatus of claim 13, wherein the protractor further comprises an annular portion and a reference portion disposed in an interior of the annular portion, the reference portion including the radial reference edge, the features disposed along the annular portion.

20. The apparatus of claim 19, wherein the intersection of the arms of the angle indicator is visibly centered in the annular portion.

21. The apparatus of claim 19, wherein the reference portion extends anteriorly away from the annular portion.

* * * * *